US012558575B1

(12) United States Patent

Bader

(10) Patent No.: US 12,558,575 B1
(45) Date of Patent: Feb. 24, 2026

(54) GUIDED ULTRASOUND FOR THE TARGETING AND TREATMENT OF TENDON DISORDERS

(71) Applicant: Lucas J. Bader, Hallandale Beach, FL (US)

(72) Inventor: Lucas J. Bader, Hallandale Beach, FL (US)

( * ) Notice: Subject to any disclaimer, the term of this patent is extended or adjusted under 35 U.S.C. 154(b) by 0 days.

(21) Appl. No.: 18/926,596

(22) Filed: Oct. 25, 2024

Related U.S. Application Data

(60) Provisional application No. 63/608,604, filed on Dec. 11, 2023.

(51) Int. Cl.
<br>*A61N 7/00* (2006.01)
<br>*A61B 8/00* (2006.01)
<br>*A61B 8/08* (2006.01)
<br>*A61N 7/02* (2006.01)
<br>*G16H 20/30* (2018.01)

(52) U.S. Cl.
<br>CPC ................ *A61N 7/02* (2013.01); *A61B 8/085* (2013.01); *A61B 8/4254* (2013.01); *A61B 8/4263* (2013.01); *A61B 8/4281* (2013.01); *A61B 8/4483* (2013.01); *A61B 8/4494* (2013.01); *G16H 20/30* (2018.01); *A61N 2007/0039* (2013.01); *A61N 2007/0052* (2013.01); *A61N 2007/0056* (2013.01); *A61N 2007/0078* (2013.01); *A61N 2007/0082* (2013.01)

(58) Field of Classification Search
<br>CPC ... A61B 8/4263; A61B 8/4254; A61B 8/4483; A61B 8/4494
<br>See application file for complete search history.

(56) References Cited

U.S. PATENT DOCUMENTS

| | | | |
|---|---|---|---|
| 8,197,409 B2 | 6/2012 | Foley et al. | |
| 8,652,157 B2 | 2/2014 | McCormack et al. | |
| 10,279,201 B2 * | 5/2019 | Hyde ..................... | G16H 40/63 |
| 10,314,688 B2 | 6/2019 | Shepard et al. | |
| 11,511,017 B2 | 11/2022 | Shepard et al. | |

(Continued)

FOREIGN PATENT DOCUMENTS

WO    WO-2017182344 A1 * 10/2017  ........... A61B 8/4488

*Primary Examiner* — Colin T. Sakamoto
<br>(74) *Attorney, Agent, or Firm* — John Rizvi; John Rizvi, P.A.—The Patent Professor®

(57) ABSTRACT

A wearable ultrasound apparatus for the diagnosis and treatment of pathological tendon tissue is provided including a flexible transducer array housing comprising a plurality of transducer sub-arrays further comprised of a plurality of piezoelectric transducer elements. Wherein the flexible transducer housing includes at least two or more transducer sub-arrays the placed within adjacent segments, each segment separated by a flexible hinge that allows for contouring of the array to a patient's anatomy. The bottom side of the flexible transducer housing being secured to an acoustic impedance layer and the bottom side of the acoustic impedance layer being secured to an adhesive layer. The adhesive layer holds the flexible transducer housing and the entirety of its contents onto a patient's skin for imaging. The wearable ultrasound diagnosis and therapeutic apparatus is multifunctional with improved real time accuracy in targeting of pathological tendon tissue that is modular, flexible, wearable, and user and patient friendly.

14 Claims, 6 Drawing Sheets

(56)        References Cited

U.S. PATENT DOCUMENTS

| | | | |
|---|---|---|---|
| 2007/0078345 A1* | 4/2007 | Mo | A61B 8/12 |
| | | | 600/459 |
| 2008/0275481 A1 | 11/2008 | Scarpone | |
| 2012/0070418 A1 | 3/2012 | Kopyov | |
| 2012/0197118 A1* | 8/2012 | Lisiecki | A61B 8/04 |
| | | | 600/438 |
| 2013/0116561 A1* | 5/2013 | Rothberg | A61B 8/4477 |
| | | | 600/459 |
| 2017/0311924 A1* | 11/2017 | Sudol | A61B 8/4254 |
| 2018/0168544 A1* | 6/2018 | Davidsen | A61B 8/4254 |
| 2020/0197039 A1 | 6/2020 | Hatch | |
| 2020/0289707 A1 | 9/2020 | Shepard et al. | |
| 2021/0059634 A1* | 3/2021 | Hamelmann | A61B 8/085 |
| 2021/0177379 A1* | 6/2021 | Kolen | A61B 8/483 |
| 2022/0000897 A1 | 1/2022 | Ning | |

* cited by examiner

GUIDED ULTRASOUND FOR THE TARGETING AND TREATMENT OF TENDON DISORDERS

CROSS-REFERENCE TO RELATED APPLICATIONS

This application claims the benefit of U.S. Provisional Patent Application Ser. No. 63/608,604, filed on Dec. 11, 2023, which is incorporated by reference herein in its entirety.

FIELD OF THE INVENTION

The present invention relates generally to medical imaging devices, and more particularly, to a wearable ultrasound device for the targeting and treatment of tendon pathologies.

BACKGROUND OF THE INVENTION

Tendinopathy (often referred to as tendinitis or tendinosis) is an overwhelmingly common tendon disorder, accounting for over thirty percent of musculoskeletal consultations. Common examples of tendinopathy include Plantar Fasciitis, Achilles Tendinitis, Rotator Cuff Tendinitis, and Lateral epicondylitis (tennis elbow). Typical symptoms associated with tendinopathy are activity related pain, focal tendon tenderness, decreased strength, and reduced movement of the affected area. Therefore, resulting in a significant disability that compromises an individuals' daily life in the areas of recreation, sporting, work, and other common daily activities.

Tendons are specialized tissue that connect muscle to bone and transmit forces generated by the muscle to bone, resulting in joint movement. However, when tendon cells experience a large volume of repetitive load, the tendon cells begin to demonstrate a more fibrochondrogenic phenotype, and therefore, the extracellular matrix that makes up the tendon is thicker, weaker, holds more water, less organized, and contains less elasticity due to a reduction of type I collagen. This is a degenerative process that aside from the symptoms mentioned, also results in the increase of vasculature and nerve ingrowths surrounding the affected tendon.

Ultrasound diagnostic apparatuses function through the transmission of ultrasound waves generated by piezoelectric elements formed in an array. These elements function similarly to tuning forks, in that, when struck with an electrical impulse, the elements vibrate at an ultrasonic frequency (20,000 Hz or higher), thereby, producing ultrasonic sound waves. The waves then propagate through a medium, whereby they are eventually reflected to the piezoelectric elements. The piezoelectric elements being struck by sound waves, are caused to vibrate once more, thus, producing voltage signals that through various processing steps, are formed into observable images.

Ultrasound diagnostic and treatment apparatuses are commonly used in a medical setting for the observation or diagnosis of pathological tissue(s), blood flow (doppler), monitoring of fetal development, vasculature, and more. Therefore, ultrasound diagnostic apparatuses are popular for their ability to display images in real-time and minimal training without the need for radiation exposure or contrast agents as used within other common forms of medical diagnostic imaging (X-ray, Computed Tomography (CT), and Magnetic Resonance Imaging (MRI)). Conventional ultrasound diagnostic apparatuses are typically comprised of an ultrasound probe, wherein within the ultrasound probe is a transducer array. Once the transducer array has obtained reflected ultrasound signals, the signals are sent to an apparatus main body that comprises a display and control board, wherein an internal processor utilizes the received signals to form an image that is exhibited to a user. These ultrasound diagnostic apparatuses lack portability as they are rather large and need to be wheeled around a hospital environment.

Accordingly, there is an established need for a portable ultrasound diagnosis and treatment device the can provide both real time accurate imaging capabilities for the targeting of pathological tendon tissue, as well as, a plurality of treatment modalities (for example, high intensity focused ultrasound (HIFU), low intensity focused ultrasound (LIFU), pulsed ultrasound cavitation therapy, and microbubble targeted drug delivery) to manage symptoms and promote tissue regeneration in a non-invasive, and end-user friendly manner.

SUMMARY OF THE INVENTION

In recent years, ultrasound diagnostic apparatuses have been designed to be portable in the form of wireless ultrasound probes and mobile displays, thus, allowing for a physician to quickly commute between ultrasound imaging procedures. Furthermore, recent technological advances have allowed for the development of small wafer-thin ultrasound transducer arrays in the form of capacitive micromachined transducers (CMUTs) and piezoelectric micromachined ultrasound transducers (PMUTs). Thus, enabling the creation of wearable ultrasound transducers or the implementation of ultrasound transducers within various medical instruments.

The present invention is directed to a wearable ultrasound diagnosis and treatment apparatus that is multifunctional with improved real time accuracy in targeting of pathological tendon tissue that is modular, flexible, wearable, and user and patient friendly.

In a first implementation of the invention, a wearable ultrasound diagnosis and treatment apparatus comprising a flexible transducer housing, wherein the flexible transducer housing includes at least two or more transducer sub-arrays each having a plurality of piezoelectric transducer elements, the sub-arrays being placed within adjacent segments, each segment separated by a flexible hinge. The bottom side of the flexible transducer housing being secured to an acoustic impedance layer and the bottom side of the acoustic impedance layer being secured to an adhesive layer. The adhesive layer holds the flexible transducer housing and the entirety of its contents onto a patient's skin for imaging. Each sub-array is operably coupled to a processor configured to receive ultrasound image data from the sub-array and generate observable images of the acquired data. Each processor operably coupled to a position sensor configured to provide a location and/or orientation of the sub-array relative to the target position and an optical marker. The wearable ultrasound diagnosis and treatment apparatus including a display communicatively coupled to each of the plurality of processors and is configured to acquire a user selection of a target tissue, acquire a user selection of an ultrasound dose, and display the ultrasound image generated by the plurality of processors based on the acquired ultrasound image data.

In a second aspect, wherein the adhesive layer can include at least one of peripheral micropores, mesh, or strategic portals.

In another aspect, wherein the adhesive layer may comprise grid lines.

In another aspect, wherein the transducer sub-array elements may be Capacitive Micromachined Ultrasound Transducers (CMUTs).

In another aspect, wherein the transducer sub-array elements may be Piezoelectric Micromachined Ultrasound Transducers (PMUTs).

In another aspect, wherein the transducer sub-array elements may be Piezocomposite Micromachined Ultrasound Transducers.

In another aspect, wherein the transducer sub-array elements may be made from a piezoelectric material such as doped lead zirconate titanate (PZT), piezo composite or other now known or later developed transducer material.

In another aspect, a receive beamformer may be located within the flexible transducer housing.

In another aspect, the receive beamformer may be communicatively coupled with the processor, wherein the receive beamformer can comprise a plurality of signal amplifiers, signal delays, phase rotators, and one or more adders.

In another aspect, the receive beamformer may be a single receive beamformer communicatively coupled with each of the transducer sub-arrays or a plurality of receive beamformers each communicatively coupled with their own transducer sub-array.

In another aspect, electronic components of the flexible transducer housing can include multiplexors for time division (multiplexing) or switches for sub-array mixing.

In another aspect, wherein the position sensors can be one of inertial measurement units (IMUs), optical, or a combination of both types.

In another aspect, wherein the position sensors may be relative or absolute position sensors.

In another aspect, wherein the flexible transducer housing may be made up of at least a Polymer (Polyethylene Terephthalate (PET), Polyimide (PL), Polyethylenenaphthalate (PEN), Polyurethane (PU), or Polydimethysiloxane (PDMS)), Acrylic (3M, VHB, 4910, or 4905), Silicone elastomer (Nusil, Elkem Silbione 4717, or Shin Etsu), Textile (NanoSan), or elastomer (polyurethanes, silicones, and acrylics).

In another aspect, wherein the display may be a touch screen.

In a second implementation of the invention, a wearable ultrasound diagnosis and treatment method comprising the placement of a sterile adhesive layer on the target area of a patient. The placement of an acoustic impedance layer atop a first area of the sterile adhesive layer. The adhesive layer holding a flexible transducer housing and the entirety of its contents onto a patient's skin for imaging. The flexible transducer housing includes a plurality of ultrasound transducer sub-arrays operably coupled to a processor. The processor is configured to receive ultrasound image data from the and generate observable images of the acquired data. The acoustic impedance layer is then repositioned to a second zone and the acquired data is generated by the processor to form an ultrasound image. Each processor is operably coupled to a position sensor configured to provide a location and/or orientation of the sub-array relative to the target position and an optical marker. The wearable ultrasound diagnosis and treatment apparatus including a display communicatively coupled to each of the plurality of processors. Wherein the display is configured to generate a three-dimensional (3D) ultrasound image, and after identification of a target tissue, receive a user input among a plurality of therapeutic ultrasound modalities for one of high intensity focused ultrasound (HIFU), low intensity focused ultrasound (LIFU), pulsed ultrasound cavitation therapy, or microbubble targeted drug delivery. The display comprises an internal processor that is configured to generate a recommendation to be displayed to a user for an acoustic impedance layer based on the user selection of a therapeutic ultrasound modality. The recommendation could be the type of acoustic impedance layer, placement of the acoustic impedance layer upon the adhesive layer grid, and ultrasound imaging parameters. The acoustic impedance layer secured to the bottom portion of the flexible transducer housing, and the therapeutic ultrasound treatment is performed by the user.

In a second aspect, wherein the adhesive layer can include at least one of peripheral micropores, mesh, or strategic portals.

In another aspect, wherein the adhesive layer may comprise grid lines.

In another aspect, wherein the transducer sub-array elements may be Capacitive Micromachined Ultrasound Transducers (CMUTs).

In another aspect, wherein the transducer sub-array elements may be Piezoelectric Micromachined Ultrasound Transducers (PMUTs).

In another aspect, wherein the transducer sub-array elements may be Piezocomposite Micromachined Ultrasound Transducers.

In another aspect, wherein the transducer sub-array elements may be made from a piezoelectric material such as doped lead zirconate titanate (PZT), piezo composite or other now known or later developed transducer material.

In another aspect, wherein the position sensors can be one of inertial measurement units (IMUs), optical, or a combination of both types.

In another aspect, wherein the position sensors can be relative or absolute position sensors.

In another aspect, wherein the flexible transducer housing may be made up of at least a Polymer (Polyethylene Terephthalate (PET), Polyimide (PL), Polyethylenenaphthalate (PEN), Polyurethane (PU), or Polydimethylsiloxane (PDMS)), Acrylic (3M, VHB, 4910, or 4905), Silicone elastomer (Nusil, Elkem Silbione 4717, or Shin Etsu), Textile (NanoSan), or elastomer (polyurethanes, silicones, and acrylics).

In another aspect, wherein the display may be a touch screen.

In another aspect, wherein the display may comprise an internal processing circuit.

In another aspect, the internal processing circuit may be configured to receive a user input for the manipulation of the generated three-dimensional (3D) ultrasound image (zoom in, zoom out, flip, or rotate) and selection of a target tissue site within the image by a user.

In a third implementation, a non-transitory computer readable medium operably connected to an internal processor, both within a display. The internal processor configured to execute instructions received from the non-transitory computer readable medium to generate a three-dimensional (3D) ultrasound image, and after identification of a target tissue, receive a user input among a plurality of therapeutic ultrasound modalities for one of high intensity focused ultrasound (HIFU), low intensity focused ultrasound (LIFU), pulsed ultrasound cavitation therapy, or microbubble targeted drug delivery. The internal generating a recommendation to be displayed to a user for an acoustic impedance layer based on the user selection of a therapeutic ultrasound modality. Wherein the recommendation includes the type of acoustic impedance layer, placement of the acoustic impedance layer upon the adhesive layer grid, and ultrasound imaging parameters. The acoustic impedance layer secured to the bottom portion of the flexible transducer housing, and the therapeutic ultrasound treatment is performed by the user.

These and other objects, features, and advantages of the present invention will become more readily apparent from the attached drawings and the detailed description of the preferred embodiments, which follow.

The term "comprising" can also encompass the terms "consisting essentially of" and "consisting of".

The term "about" encompasses a ten percent value above or below any range endpoint.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. The implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a wearable ultrasound diagnosis and treatment apparatus that is multifunctional with improved real time accuracy in targeting of pathological tendon tissue that is modular, flexible, wearable, and user and patient friendly.

Figure 1:
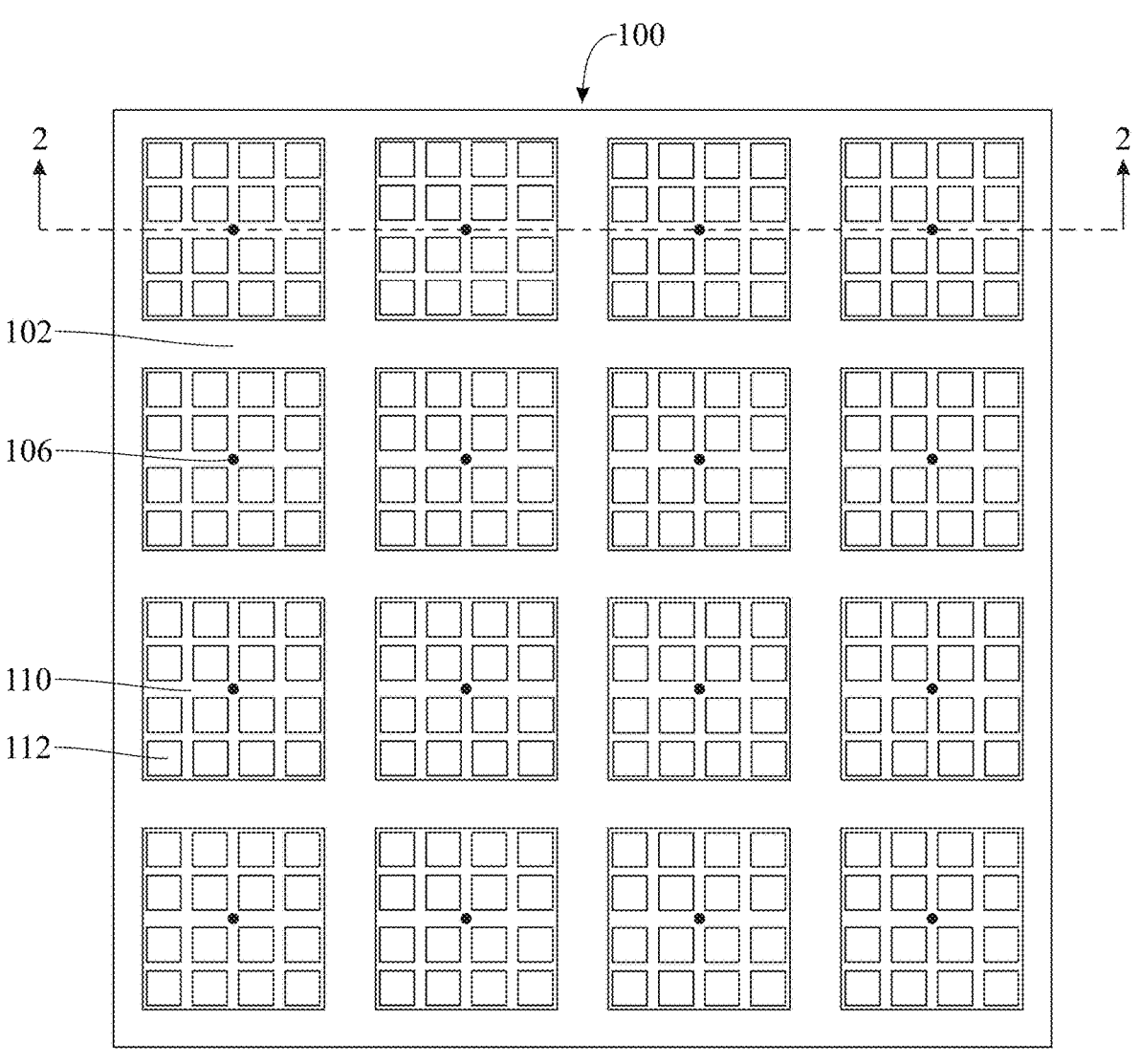
FIG. 1 presents a top perspective view of a flexible transducer housing.

Referring initially to FIG. 1, a top view of a flexible ultrasound transducer housing, hereinafter referred to as flexible housing 100A, is illustrated in accordance with a first exemplary embodiment of the present invention. As shown, flexible housing 100A is formed by a flexible substrate 102A. The flexible housing further includes a plurality of transducer sub-arrays 110A in a grid formation. Each transducer sub-array is comprised of a plurality of transducer elements 112A and a position sensor 106A. In some embodiments, the position sensors 106A may be in the form of IMU sensors, optical sensors, or a combination of both.

The flexible transducer housing is preferably made up of the following materials: Polymers (Polyethylene Terephthalate (PET), Polymide (PL), Polyethylenenaphthalate (PEN), Polyurethane (PU), or Polydimethysiloxane (PDMS)), Acrylic (3M, VHB, 4910, or 4905), Silicone elastomers (Nusil, Elkem Silbione 4717, or Shin Etsu), Textile (NanoSan), or elastomers (polyeurthanes, silicons, and acrylics)

The transducer elements 112A of the transducer sub-arrays 110A are made up of elements with differing design characteristics, thus, each sub-array has a variable operating frequency of 250 kHz to 1.5 MHz (for microbubble targeted drug delivery), 2 to 4 MHz (high intensity focused ultrasound, 1 to 3 MHz (pulsed ultrasound cavitation therapy), 15 to 60 MHz (ultrasound imaging), or 1 to 10 MHz (low intensity focused ultrasound). Each sub-array also functions at a variable output intensity of 0.5-4 W/cm$_2$ (utilized for LIFU and microbubble targeted drug delivery), 0.3 to 990 mW/cm$^2$, (ultrasound imaging) 1500-3000 W/cm$_2$ (utilized for HIFU). Each sub-array also functions at a variable pressure waveforms with amplitude of either a peak positive pressure of 20-140 MPa and peak negative pressure of −8 to −30 MPa (both positive and negative peak pressures utilized for LIFU, microbubble targeted drug delivery, and pulsed ultrasound cavitation therapy), peak pressure 0.45-5.5 MPa (ultrasound imaging), and peak pressure 5-20 MPa (HIFU).

Position sensors 106A provide an indicator of spatial location and/or orientation of each sub-array for image formation and/or beamforming. The position sensors 106A are preferably made up of either relative or absolute position sensors.

Figure 2:
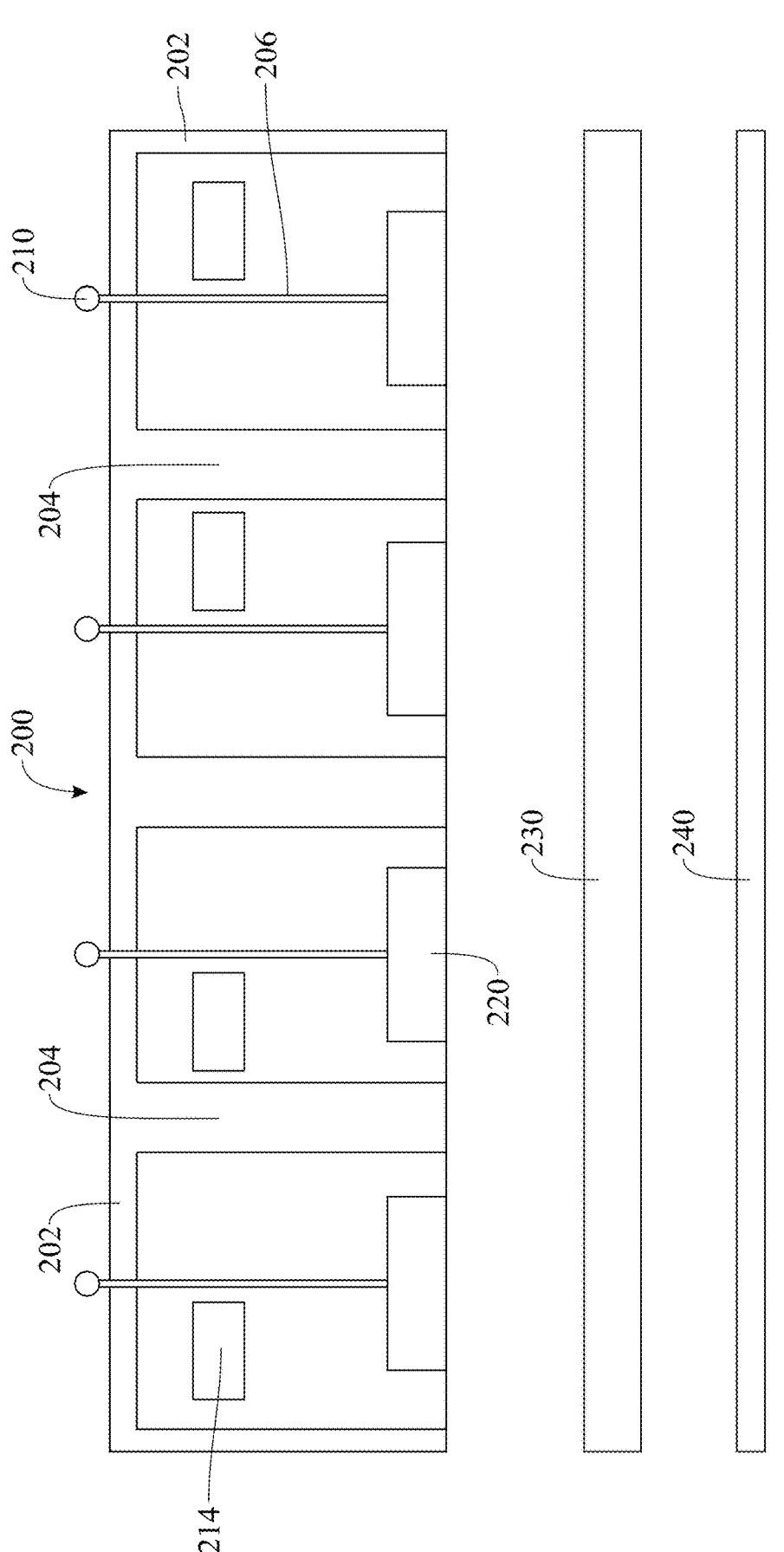
FIG. 2 presents an internal side view of the flexible transducer housing of FIG. 1.

Now referring to FIG. 2, an internal side view of the flexible ultrasound transducer array, hereinafter referred to as transducer array 200B, is illustrated in accordance with a first exemplary embodiment of the present invention. As presented, transducer array 200B is held within flexible transducer housing 202B, wherein between each transducer sub-array 220B are flexible hinges 204B. While the sub-arrays are rigid, the flexible hinges 204B and flexible transducer housing 202B allow for the contouring of transducer array 200B to patient anatomy. The sub-arrays are each communicatively couple with a processing control, hereinafter referred to as processor 214B, position sensor 206B, and optical marker 210B. At the bottom side (side opposite the optical markers 210B) of transducer array 200B is the acoustic coupling layer, hereinafter referred to as impedance layer 230B. FIG. 2 further presents adhesive layer 240B, physically coupled to the bottom side of impedance layer 230B for securing the transducer array 200B to a patient's anatomy.

Figure 3A:
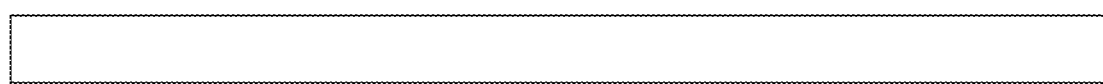
FIG. 3a presents a neutral acoustic impedance layer.
Figure 3B:
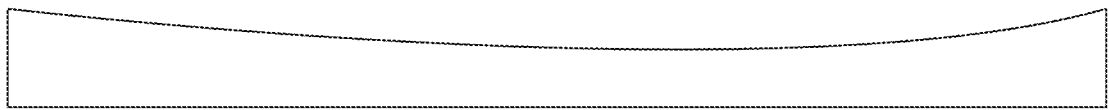
FIG. 3b presents a convex acoustic impedance layer.
Figure 3C:
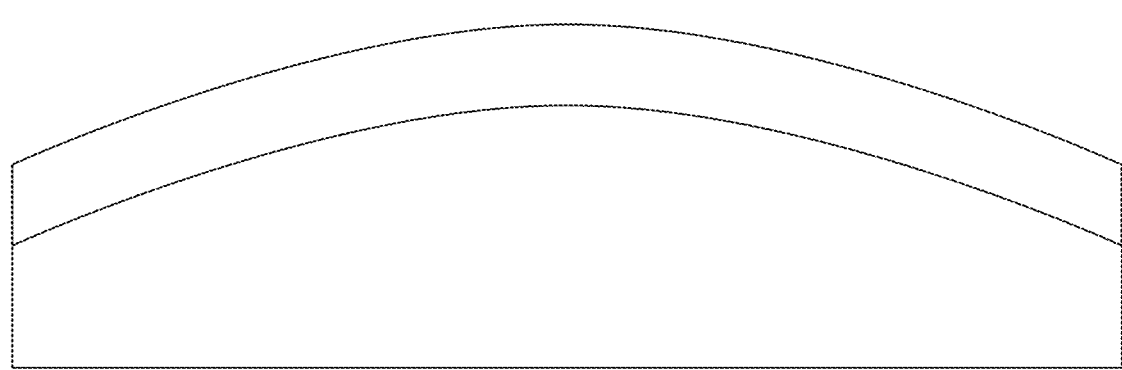
FIG. 3c presents a concave acoustic impedance layer.

Now referring to FIGS. 3a through 3c, the figures presented show the varying forms of the acoustic impedance layer. The forms being neutral (3a), convex (3b), and concave (3c). The present invention offers a multimodality function, wherein diagnostic imaging is initially performed for the identification of a target tendon tissue by a user. For this modality, a neutral or concave acoustic impedance layer is preferred. After the target tendon tissue has been identified and selected by a user, the internal processor (not pictured) of the display (not pictured) generate a recommendation to the user for next treatment steps. The therapeutic modalities of the present invention are HIFU, LIFU, microbubble targeted drug delivery, or pulsed ultrasound cavitation therapy.

The modality of HIFU produces a high intensity focused ultrasound beam that outputs a highly intense ultrasound beam that can be precisely focused on a target site. This high intensity beam results in an internal temperature increase of the targeted tissue. Therefore, the therapeutic modality of HIFU is utilized for tissue ablation of the tendon, nerves, and surrounded vasculature. Additionally, the preferred acoustic impedance layer is the neutral or concave acoustic impedance layer presented in FIG. 3a or 3c. Depending on patient's natural anatomy, this orients the transducer elements toward each other, thereby, resulting in a summation of the transmitted ultrasound waves to a small radius. This allows for the targeting of a small radius of tissue and is preferred when the physician aims to avoid damaging surround tissues that are not of interest for treatment.

The modality of LIFU produces a low intensity focused ultrasound beam that outputs a low intensity ultrasound beam. This is primarily utilized for tissue strengthening or regeneration, as well as, neuromodulation, or microbubble cavitation. The method of neuromodulation is beneficial for reduction of pains associated with the pathological tissue of interest, whereas microbubble cavitation allows for the directing of therapeutic agents to a target of interest by the formation of pores in the membranes of cells. This modality of therapeutic ultrasound utilizes the neutral, convex, or concave acoustic impedance layers of FIGS. 3a, 3b, and 3c.

The modality of pulsed ultrasound cavitation therapy outputs short, intense bursts of acoustic energy to produce controlled microbubble or bubble cloud formation. The vigorous expansion and collapse of these microbubbles mechanically homogenizes cells. Pulsed ultrasound cavitation therapy is non-thermal and distinct from thermal ablation. The preferred acoustic impedance layers are the neutral or concave acoustic impedance layers presented in FIGS. 3a and 3c.

Figure 4:
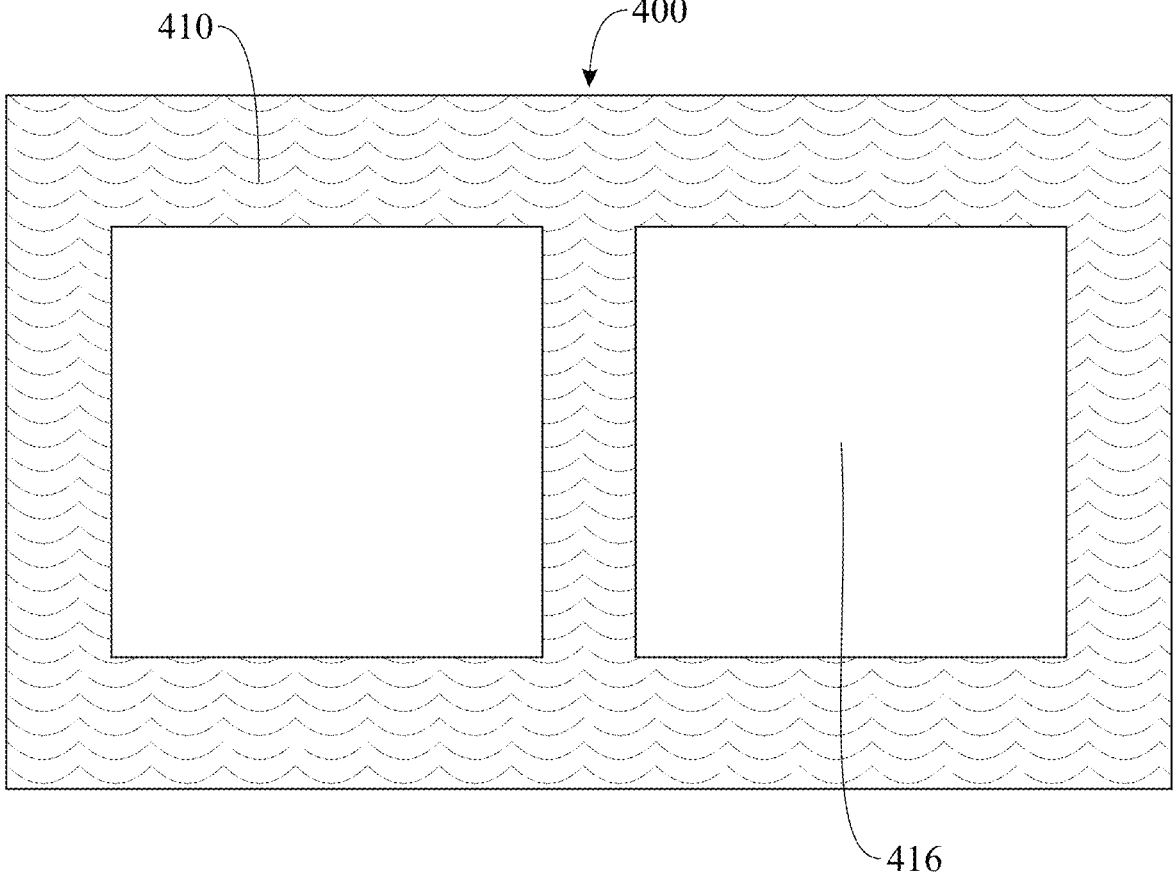
FIG. 4 presents a top perspective of an adhesive layer in accordance with a first embodiment of the present invention.

Now referring to FIG. 4, the figure presents a closer view of the adhesive layer 400C. This adhesive layer includes areas for the acoustic impedance layer (230B of FIG. 2) 416C, wherein the transducer sub-arrays of FIGS. 1 and 2 are placed. Furthermore, the adhesive layer includes an outer periphery with perforations 410C. The perforations allow for a physician to perform a therapeutic injection, debridement, or other procedure with a needle or other device if needed, through the adhesive layer placed upon the target tissue site.

Figure 5:
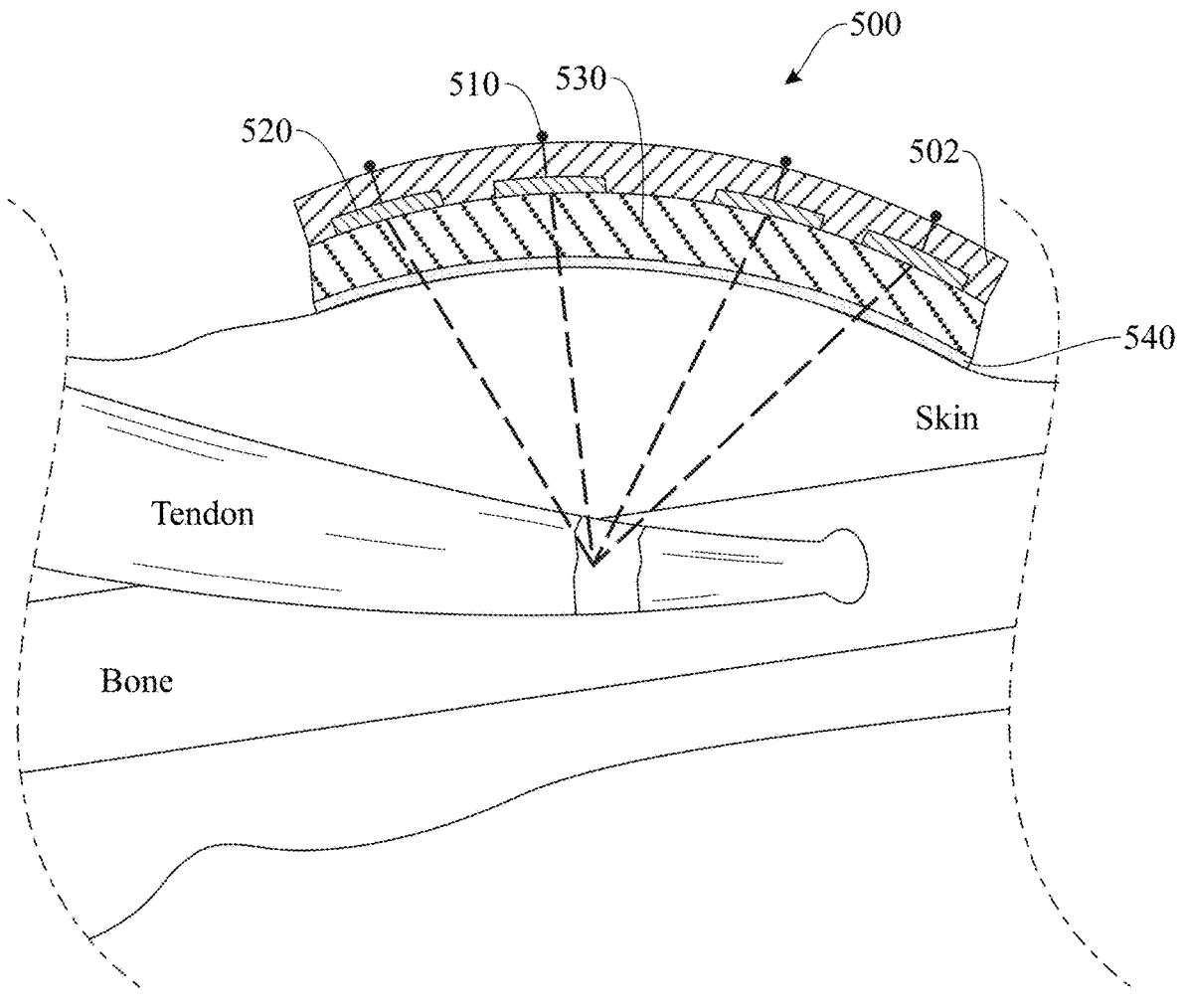
FIG. 5 presents a conceptual diagram of the wearable ultrasound transducer apparatus coupled with a neutral impedance layer for the diagnosis and treatment of a tendon.

Now referring to FIG. 5, is a diagram presenting the use of a neutral acoustic impedance layer (as presented in FIG. 3a) for the diagnostic imaging and treatment of target tendon tissue. As depicted within the figure, the transducer array 500D is coupled to the surface of a patient's anatomy, wherein sub-arrays 520D transmit ultrasound waves into the patient to be reflected and formed into clinically relevant ultrasound images, whereby, the user may identify pathological tendon tissues for diagnosis. Subsequently, each sub array outputs a high intensity or low intensity ultrasound beam with the ultrasound beam converging to the focal point in the region of interest. As can be seen in FIG. 5, the flexible transducer housing 502D can be seen as contoured to the surface of the patient's anatomy. Furthermore, the transducer array is shown to comprise optical markers 210B and coupled to acoustic impedance layer 530D on the side of the flexible transducer 502D that is opposite that of the side comprising optical markers 210B. Lastly, for the securement of the ultrasound transducer array 500D to the patient's anatomy, the adhesive layer 540D is clearly shown to be physically coupled with the bottom side of the acoustic impedance layer 530D.

Figure 6:
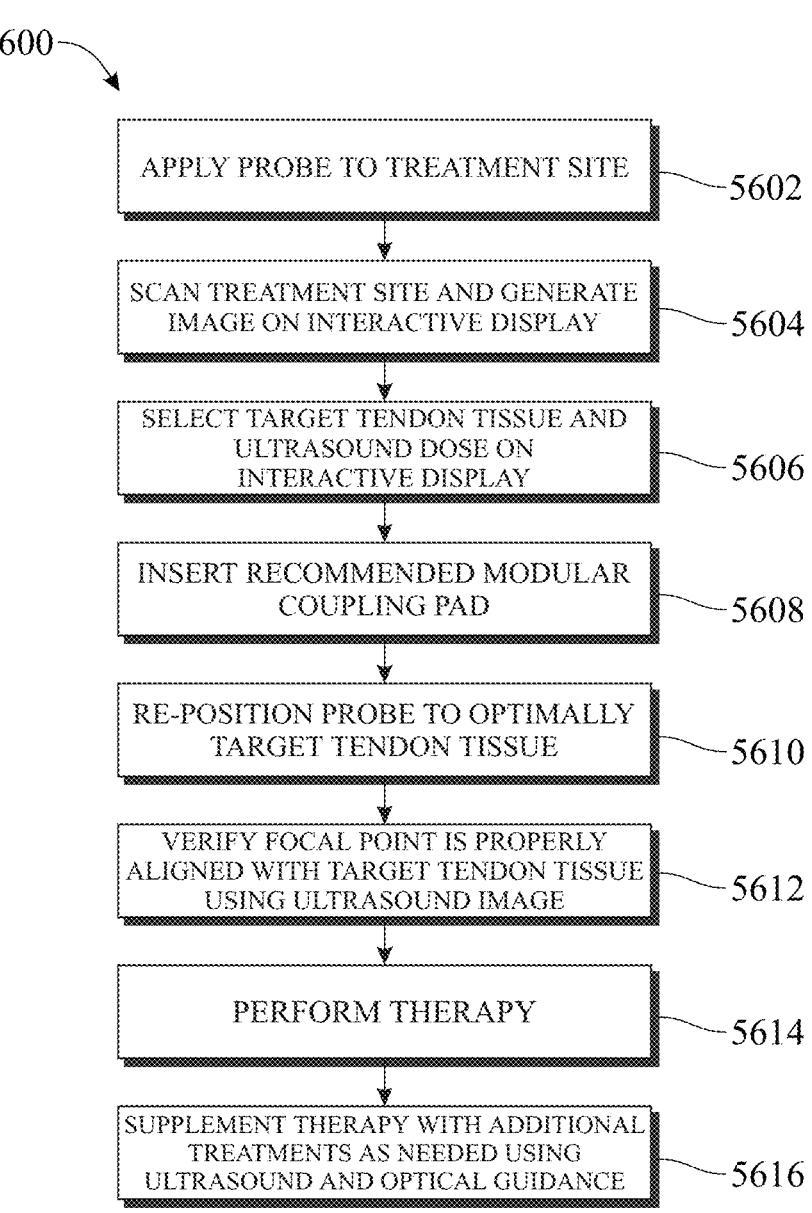
FIG. 6 presents a flow chart of the diagnosis and treatment method in accordance with a first embodiment of the present invention.

Lastly, referring to FIG. 6, the figure presents a flow-chart comprising a plurality of method steps 600E for the performance of an ultrasound diagnostic and therapeutic imaging procedure in accordance with a first embodiment. The steps are as follows: step s602E is to apply the wearable ultrasound transducer array the patient's anatomy at a target site, step s604E is the imaging step in which ultrasound image data is acquired and rendered as a three-dimensional (3D) image on an interactive display (not pictured), step s606E comprises a user selected a target tissue within the rendered (3D) image and the selection of an ultrasound dose (modality) for the treatment of the selected target site, step s608E comprises the selection of an acoustic impedance layer by the internal processor (not pictured) that is within the interactive display (not pictured) based on the ultrasound dose (modality) selected, step s610E involves the repositioning of the ultrasound transducer array in response to the feedback received by the optical markers and position sensors, step s612E is the verification of the proper alignment and positioning of the transducer array so that the focal point is properly aligned with the selected tendon tissue, step s614E comprises the application of the selection ultrasound dose (modality) to the target tendon site, and lastly, step s616E is the implementation of additional treatment methods as needed using ultrasound and optical guidance. As previously mentioned, additional treatment methods include the injection of therapeutic agents to the selected target tissue site.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A wearable ultrasound diagnosis and treatment apparatus comprising:
   a flexible transducer housing, wherein the flexible transducer housing includes at least two or more transducer sub-arrays each having a plurality of piezoelectric transducer elements, the sub-arrays being placed within adjacent segments, each segment separated by a flexible hinge;
   an acoustic impedance layer positioned on a lower side of the flexible transducer housing;
   an adhesive layer secured to the acoustic impedance layer;

wherein each sub-array is operably coupled to:

a processor configured to receive ultrasound image data from the sub-array and generate observable images of the ultrasound image data;

each processor being communicatively coupled to:

a position sensor configured to provide a location and/or orientation of the sub-array relative to a target position; and an optical marker;

a display, communicatively coupled to each of the plurality of processors, configured to:

acquire user selection of target tissue and ultrasound dose, and display ultrasound image of acquired ultrasound image data.

2. The wearable ultrasound diagnosis and treatment apparatus of claim 1, wherein the adhesive layer includes at least one of peripheral micropores, mesh, or strategic portals.

3. The wearable ultrasound diagnosis and treatment apparatus of claim 1, wherein the adhesive layer comprises grid lines.

4. The wearable ultrasound diagnosis and treatment apparatus of claim 1, wherein the transducer sub-array elements are Capacitive Micromachined Ultrasound Transducers (CMUTs).

5. The wearable ultrasound diagnosis and treatment apparatus of claim 1, wherein the transducer sub-array elements are Piezoelectric Micromachined Ultrasound Transducers (PMUTs).

6. The wearable ultrasound diagnosis and treatment apparatus of claim 1, wherein the transducer sub-array elements are Piezocomposite Micromachined Ultrasound Transducers.

7. The wearable ultrasound diagnosis and treatment apparatus of claim 1, further comprising a receive beamformer located within the flexible transducer housing.

8. The wearable ultrasound diagnosis and treatment apparatus of claim 7, wherein the receive beamformer is communicatively coupled with the processor, and wherein the receive beamformer comprises a plurality of signal amplifiers, signal delays, phase rotators, and one or more adders.

9. The wearable ultrasound diagnosis and treatment apparatus of claim 7, wherein the receive beamformer is a single receive beamformer communicatively coupled with each of the transducer sub-arrays or a plurality of receive beamformers each communicatively coupled with their own transducer sub-array.

10. The wearable ultrasound diagnosis and treatment apparatus of claim 1, wherein electronic components of the flexible transducer housing include multiplexors for time division (multiplexing) or switches for sub-array mixing.

11. The wearable ultrasound diagnosis and treatment apparatus of claim 1, wherein the position sensors are one of inertial measurement units (IMUs), optical, or a combination of both types.

12. The wearable ultrasound diagnosis and treatment apparatus of claim 1, wherein the position sensors are relative or absolute position sensors.

13. The wearable ultrasound diagnosis and treatment apparatus of claim 1, wherein the flexible transducer housing is made up of at least a Polymer, Acrylic, Silicone elastomer, Textile, or elastomer.

14. The wearable ultrasound diagnosis and treatment apparatus of claim 1, wherein the display is a touch screen.

* * * * *